US005861251A

United States Patent [19]
Park et al.

[11] Patent Number: 5,861,251
[45] Date of Patent: Jan. 19, 1999

[54] LYOPHILIZED REAGENT FOR POLYMERASE CHAIN REACTION

[75] Inventors: Han-Oh Park; Jae-Jong Kim, both of Taejon, Rep. of Korea

[73] Assignee: Bioneer Corporation, Rep. of Korea

[21] Appl. No.: 732,662

[22] Filed: Oct. 15, 1996

[51] Int. Cl.$^6$ ............... C12P 19/34; C12Q 1/68; C12N 9/96; C07H 5/04

[52] U.S. Cl. ............ 435/6; 435/91.2; 435/188; 536/24.33; 935/77; 935/78

[58] Field of Search ............... 435/188, 6, 40.5, 435/91.2, 71.9, 199; 536/24.33, 18.7, 25.6; 424/94.5; 935/77, 78

[56] References Cited

U.S. PATENT DOCUMENTS

| | | | |
|---|---|---|---|
| 5,049,490 | 9/1991 | Sutherland et al. | 435/6 |
| 5,338,671 | 8/1994 | Scalice et al. | 435/91.2 |
| 5,556,771 | 9/1996 | Shen et al. | 435/91.2 |

OTHER PUBLICATIONS

Colaco, C., Sen, S., Thangavelu, M., Pinder, S., and Roser, B., *Extraordinary Stability of Enzymes Dried in Trehalose: Simplified Molecular Biology*, Bio/Technology 10:1007–1011, 1992.

Madej, R., and Scharf, S., Basic Equipment and Supplies, PCR Protocols: A Guide to Methods and Applications, eds. M.A. Innis, D.H. Gelfand, J.J. Sninsky, and T.J. White, Academic Press, Inc., San Diego, CA, Chapter 55, pp. 455–459, 1990.

DuPont Biotechnology Update, Winter Issue, p. 3, 1994.

Ogden, R.C. and Adams, D.A., Electrophoresis in Agarose and Acrylamide Gels, Methods in Enzymology 152:61–65, 1987.

Kaneko, S. et al. *Detection of Serum Hepatitis B Virus DNA in Patients with Chronic Hepatitis Using the Polymerase Chain Reaction Assay*, Proc.Natl.,Acad.Sci. USA, 86:312–316 (1989).

Nelson, D.L. et al., *Alu Polymerase Chain Reaction: A Method for Rapid Isolation of Human–Specific Sequences from Complex DNA Sources*, Proc.Natl.,Acad.Sci. USA; 86:6686–6690 (1989).

Gyllensten, U.B. and Ehrlich, H.A., *Generation of Single–Stranded DNA by the Polymerase Chain Reaction and Its Application to Direct Sequencing of the HLA–DQA Locus*, Proc.Natl.Acad.Sci. USA, 85:7652–7656 (1988).

Frohman, M.A. et al., *Rapid Production of Full–Length cDNAs from Rare Transcripts: Amplification Using a Single Gene–Specific Oligonucleotide Primer*, Proc.Natl.Acad.Sci. USA, 85:8998–9002 1988).

Zhou, H. et al., *Universal Immuno–PCR for Ultra–Sensitive Target Protein Detection*, Nucleic Acids Res., 21(25):6038–6039 (1993).

Kwok, S. et al., *Enzymatic Amplification of HTLV–I Viral Sequences from Peripheral Blood Mononuclear Cells and Infected Tissues*, Blood, 72:1117–1123 (1988).

Rayfield, M. et al., *Mixed Human Immunodeficiency Virus (HIV) Infection in an Individual: Demonstration of Both HIV Type 1 and Type 2 Proviral Sequences by Using Polymerase Chain Reaction*, J. Infect.Dis., 158:1170–1176 (1988).

Ballabio, A. et al., *PCR Test for Cystic Fibrosis Deletion*, Nature, 343:220 (1990).

Kwok, S. and Higuchi, R., *Avoiding False Positives with PCR*, Nature, 339:237–238 (1989).

*Primary Examiner*—David M. Naff
*Assistant Examiner*—Janet M. Kerr
*Attorney, Agent, or Firm*—Darby & Darby

[57] ABSTRACT

The present invention provides a process for preparing a ready-to-use reagent for PCR, which comprises the steps of adding the stabilizer, glucitol or glucose, to an aqueous polymerase chain reaction(PCR) mixture containing a reaction buffer, $MgCl_2$, dNTPs, a DNA polymerase, the water soluble dye, bromophenol blue, xylene cyanole, bromocresol red or cresol red, a primer, and optionally, ddATP, ddCTP, ddGTP, or ddTTP, and then lyophilizing thereof. The ready-to-use PCR reagent of the present invention leads to a simplification of multi-step PCR manipulation, an increase of heat stability of the reaction mixture, prevention of carry-over contamination, and improved credibility of experiments. The ready-to-use PCR reagent can be applied as a kit for analysis of DNA sequence or for diagnosis of diseases.

2 Claims, 3 Drawing Sheets

LYOPHILIZED REAGENT FOR POLYMERASE CHAIN REACTION

BACKGROUND OF THE INVENTION

1. Field of the Invention

The present invention relates to an instant reagent for polymerase chain reaction, more specifically, to an instant reagent for DNA polymerase chain reaction which is stabilized and lyophilized to ease DNA amplification, sequencing and diagnosis of disease.

2. Description of the Prior Art

DNA polymerase chain reaction(hereinafter referred to as "PCR") allows the DNA sequence at a specific region of a genome to be amplified by more than a millionfold, provided that at least part of its nucleotide sequence is already known. Portions of the sequence that surround the region to be amplified are used to design two synthetic DNA oligonucleotides, one complementary to each strand of the DNA double helix. These oligonucleotides serve as primers for in vitro DNA synthesis, which is catalyzed by a DNA polymerase, and they determine the ends of the final DNA fragment that is obtained. Each cycle of the PCR requires denaturation to separate two strands of the DNA double helix, annealing for specific hybridization to complementary DNA sequences, and extension for synthesis of DNA. For effective amplification, 30 to 40 cycles of reaction are required.

In conclusion, the PCR by which a specific nucleotide sequence can be amplified in vitro from the genomic DNA, enables the detection of a specific DNA sequence and the acquisition of the DNA fragment of interest in large quantities in a short period of time.

The PCR technique has been utilized in a wide range of life sciences, such as in the detection of genes associated with genetic diseases(see: Suzuki, Y. et al., Anal. Biochem., 192:82–84(1991); Gibbs, R. A. et al., Nucleic Acids Res., 17:2374–2448(1989); Ballabio, A. et al., Nature, 343:220 (1990)); in the detection and expression of a specific mRNA by way of cDNA amplification by employing reverse transcription-PCR(RT-PCR) and RACE(rapid amplification of cDNA end) methods (see: Rappolee, D. A. et al., Science, 241:708–712 (1991); Frohman, M. A. et al., Proc. Natl. Acad. Sci., U.S.A., 85:8998–9002(1988)); in direct nucleotide sequencing from the amplified product of DNA(see: Gyllensten, U. B. et al., Proc. Natl. Acad. Sci., U.S.A., 85:7652–7657(1988)); in the analysis of VNTR(various number of tandem repeat) (see: Ali, S. et al., Nucleic Acids Res., 16:8487–8496(1988)); and, in genetic mapping(see: Nelson, D. L. et al., Proc. Natl. Acad. Sci., U.S.A., 86:6686–6690(1989)). In addition, it has been also utilized in the diagnosis of a variety of diseases, such as HTLV-I (human T-cell lymphoma/leukemia virus type I) (see: Kwok, S. et al., Blood, 72:1117–1123(1988)), HIV(human immunodeficiency virus)(see: Ou, C. Y. et al., J. Infect. Dis., 158:1170–1176(1988)) and HBV(hepatitis B virus) (see: Kaneko, S. et al., Proc. Natl. Acad. Sci., U.S.A., 86:312–316 (1989)), and currently its usefulness becomes more and more widespread.

Furthermore, applications of said PCR technique, e.g., DD-PCR(differential display-PCR) and Immuno-PCR(see: Hong, Z. et al., Nucleic Acids Res., 21:6038–6039(1993)) have been developed, which permit detection of only a small portion of RNA or DNA in question not detectable using currently available methods.

In the amplification of nucleic acids by the PCR technique, every component of the reaction mixture for PCR, i.e., a template DNA, primers, reaction buffer, $MgCl_2$, KCl, dNTPs (dATP, dCTP, dGTP and dTTP) and DNA polymerase, must be mixed in a step-wise fashion or simultaneously at the initial step, prior to initiating the reaction. Accordingly, it has been cumbersome to add and mix the trace amounts of each component in a separate manner for every test sample, which results in frequent experimental errors. Especially when numerous samples are to be analyzed in a short period of time, the inefficiency and accompanied errors have become serious obstacles in the experiments.

Moreover, it has been also known that the aerosol which develops when sample loading buffer is added to the PCR product, in the process of analyzing PCR product, frequently induces carry-over contamination(see: Kwok, S. et al., Nature, 339:237–238(1989)) and leads to a false positive response, which has been an important problem to be solved, especially when used in diagnosis of diseases.

SUMMARY OF THE INVENTION

In accordance with the present invention, it has been found that an instant PCR reagent of the invention can be utilized for DNA amplification without any worries for experimental errors, and also found that the reagent which further comprises sedimenting agent and water-soluble dye, can be free from the worry of carry-over contamination caused by aerosol.

A primary object of the present invention is, therefore, to provide an instant reagent for PCR which is prepared by adding stabilizer to an aqueous reaction mixture and lyophilizing thereof.

The other object of the invention is to provide the use of the reagent for analysis of nucleotide sequence and for diagnosis of diseases.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
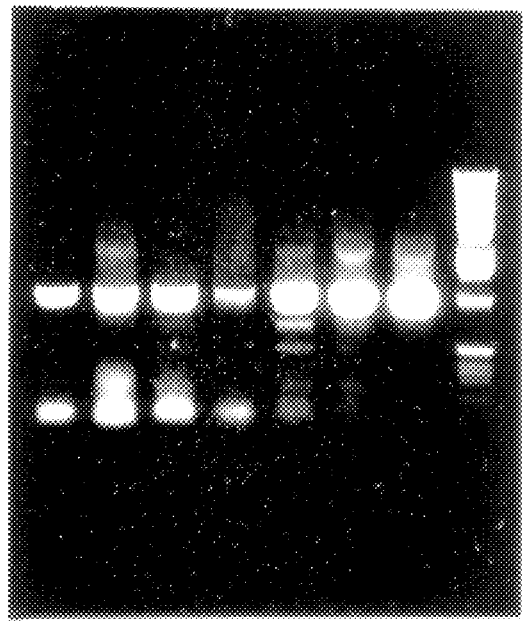
FIG. 1 is a photograph showing agarose gel electrophoresis pattern of the PCR products amplified with conventional aqueous PCR mixtures containing stabilizers.

In general, an instant reagent for PCR(hereinafter referred to as "PCR reagent") of the present invention is prepared by freeze-drying a conventional aqueous reaction mixture which consists of a reaction buffer, $MgCl_2$, dNTPs and a DNA polymerase; and, depending on the purpose of the use, the lyophilized reagent may be put to practical use together with other combinations of components: e.g., distilled water, primers and a template DNA; distilled water and a template DNA; or, distilled water only. For example, for the diagnosis of HIV, HBV and TB(tuberculosis), the PCR reagent may be mixed with their genomic DNA/RNA and complementary primers; and, for DNA sequencing, it may be mixed with the universal or appropriate primers.

It has been well known that: materials such as gelatin, bovine serum albumin(BSA), ammonium sulfate or Thesit etc., stabilize a DNA polymerase and dNTPs, and non-ionic surfactants such as NP40 and Tween 20 etc., improve the reactivity of the PCR mixture(see: Saiki, R. K. et al., Science, 239:487–491(1988)). The inventors, however, determined that ammonium sulfate may affect on the level of PCR process seriously when it is employed in lyophilized PCR reagent. Accordingly, PCR reagent of the invention preferably comprises a stabilizer such as gelatin, BSA, Thesit (polyoxyethylene-9-lauryl ether), PEG-8000 (polyethyleneglycol-8000) or polyol(e.g., glycerol, glucose, mannitol, galacitol, glucitol and sorbitol), most preferably, polyol, since polyol is determined to play a role as a sedimenting agent.

The PCR reagent of the invention may further comprise a sedimenting agent or a water-soluble dye in the presence/absence of stabilizer. As described above, the inventors determined that polyol plays dual role as a stabilizer and a sedimenting agent, and most preferably, glucitol which is a kind of polyol, may be added to the reagent. As a water-soluble dye, bromophenol blue, xylene cyanole, bromocresol red or cresol red etc., may be added to the reagent. The water-soluble dye facilitates identifying complete mixing of the PCR reagent and a test sample, and saves the trouble of adding a sample loading buffer which is required for analysis of PCR products, thereby preventing the carry-over contamination.

The PCR reagent of the invention provides advantages as follows: first, it simplifies the multi-step PCR manipulation in which every component of the reaction mixture for PCR is to be added to each of test samples; secondly, it increases the heat stability of the reaction mixture; thirdly, it prevents carry-over contamination by skipping the step of adding the sample loading buffer which is necessary for analysis of PCR products; fourthly, it improves credibility for PCR in diagnosis of diseases and in performance of repeated experiments, by excusing any possibility of committing experimental errors caused by mispipetting.

The PCR reagent of the present invention can be developed as a kit for analysis of nucleotide sequence or diagnosis of diseases, and for DNA amplification of a specific region of genome as well.

The present invention is further illustrated in the following examples, which should not be taken to limit the scope of the invention.

EXAMPLE 1

Conventional PCR Employing an Aqueous PCR Mixture

The inventors first carried out a polymerase chain reaction (PCR) employing a conventional aqueous PCR mixture as a control and attempted to test effects of various factors which may have an effect on the level of PCR, e.g., lyophilization, the addition of stabilizer, sedimenting agent and water-soluble dye, to prepare the PCR reagent of the invention.

In order to amplify 1 kb DNA fragment corresponding to a specific region of bacteriophage λDNA, primers P1(20 mer) of 5'-CGCCACGACGATGAACAGAC-3' and P2(18 mer) of 5'CCACGGGTAAAGTTGGGC-3' were synthesized. A PCR mixture was prepared to contain 10 mM of Tris-HCl(pH 8.3), 40 mM of KCl, 1.5 mM of $MgCl_2$, 1 mM of DTT, 50 mg/ml of BSA, 250 μM of each dNTP, 50 pmoles of each primer P1 and P2, and 1 ng of λDNA in a final volume of 0.05 ml. Each cycle of PCR needed denaturation (94° C., 1 min), annealing(54° C., 1 min) and extension(72° C., 1 min), and 30 cycles were required for effective amplification. The PCR products thus amplified were electrophoresed on 1% (w/v) agarose gel; and, only one band migrated at the position of about 1 kb. Accordingly, it was clearly demonstrated that 1 kb DNA fragment was amplified from the PCR mixture.

EXAMPLE 2

Effect of Stabilizer on PCR

To determine the effect of stabilizer on PCR, stabilizers, e.g., 20 mM of ammonium sulfate, 4% of glycerol, 20 mM of glucitol, 20 mM of ammonium sulfate and 4% of glycerol, 0.1% of PEG-8000 and 0.1% of Thesit(Boeringer Mannheim, Germany) were added to the conventional aqueous PCR mixture employed in Example 1 and then PCR followed in an analogous manner as in Example 1. The PCR products thus amplified were electrophoresed on 1% (w/v) agarose gel(see: FIG. 1).

In FIG. 1, lanes 1 to 6 are PCR products amplified by the PCR mixtures containing 20 mM ammonium sulfate, 4% glycerol, 20 mM glucitol, 20 mM ammonium sulfate and 4% glycerol, 0.1% PEG-8000 and 0.1% Thesit, respectively; lane 7 is control(PCR product amplified by a conventional PCR mixture); and, lane M is 1 kb ladder as molecular marker. As shown in FIG. 1, all the lanes except for lane 4 revealed 1 kb DNA fragment of interest. Accordingly, it could be concluded that performance of PCR is not affected by the addition of stabilizers such as ammonium sulfate, glycerol, glucitol, PEG-8000 or Thesit, provided that both ammonium sulfate and glycerol are not added to the mixture simultaneously.

EXAMPLE 3

Effect of Lyophilization on PCR

To determine the effect of lyophilization on PCR, 20 μl of PCR mixtures prepared in Example 2, were quick-frozen at −70° C. and freeze-dried by employing lyophilizer(Ilshin Engineering, Korea). The resulting lyophilized PCR mixtures were dissolved thoroughly with 20 μl of distilled water and PCR was carried out analogously as in Example 1.

Figure 2:
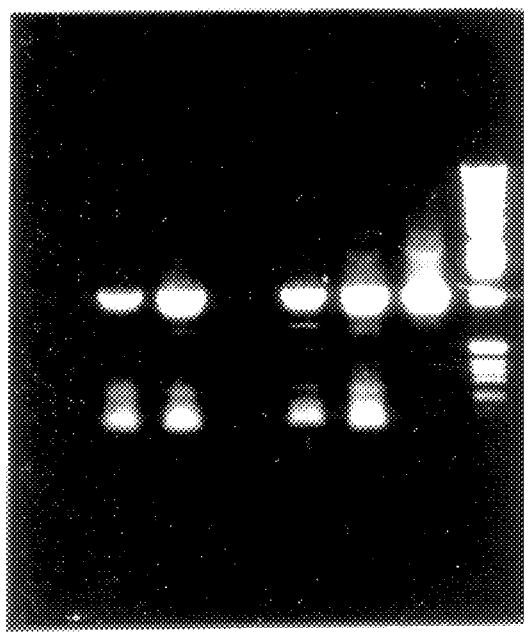
FIG. 2 is a photograph showing agarose gel electrophoresis pattern of the PCR products amplified with lyophilized PCR mixtures containing stabilizers.

FIG. 2 is a photograph showing agarose gel electrophoresis pattern of the PCR products amplified as above, where the samples loaded on each lane are identical with those of FIG. 1. As shown in FIG. 2, all the lanes except for lanes 1 and 4 both of which include ammonium sulfate, showed 1 kb DNA fragment of interest. Accordingly, it is clearly determined that: lyophilization does not have an effect on PCR, provided that ammonium sulfate is not added to the PCR mixture.

EXAMPLE 4

Determination of Heat Stability of the Lyophilized PCR Mixture Containing Stabilizer(I)

In order to examine heat stability of the lyophilized PCR mixture containing stabilizer, the PCR mixtures which were freeze-dried and provided high level of PCR in Example 3 were subject to standing at 50° C. for 62 hrs, and PCR was carried out in the presence/absence of a stabilizer.

Figure 3:
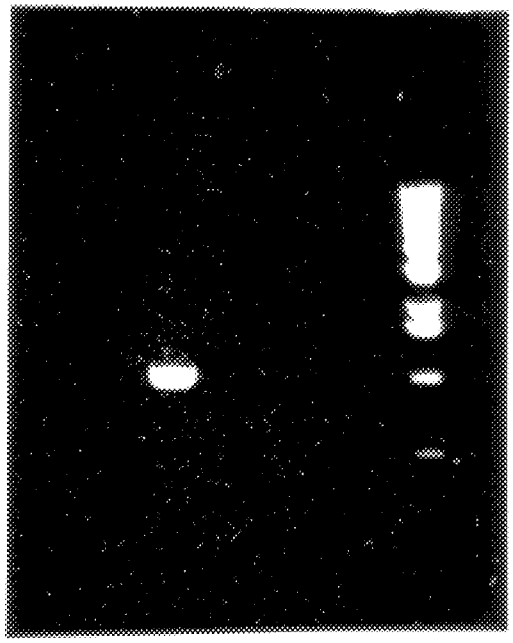
FIG. 3 is a photograph showing agarose gel electrophoresis pattern of the PCR products amplified with lyophilized PCR mixtures containing stabilizers after storage at 50° C. for 62 hrs.

FIG. 3 is a photograph showing agarose gel electrophoresis pattern of the PCR products amplified as described above. In FIG. 3, lanes 1 to 4 are PCR products amplified by PCR mixtures containing 4% glycerol, 20 mM glucitol, 0.1% PEG-8000 and 0.1% Thesit, respectively; lane 5 is a PCR product amplified using a conventional PCR mixture in the absence of stabilizer(control); and, lane M is a 1 kb ladder as a molecular marker. As shown in FIG. 3, lane 2 which represented a reaction mixture containing 20 mM glucitol revealed a distinct band corresponding to the 1 kb DNA fragment of interest, and while lanes 1, 3 and 4 showed a faint band only. Accordingly, it was determined that: the addition of stabilizer improves heat stability of PCR; and, the lyophilized PCR mixture containing 20 mM glucitol provides a highly improved heat stability.

EXAMPLE 5

Determination of Heat Stability of the Lyophilized PCR Mixture Containing Stabilizer (II)

Figure 4:
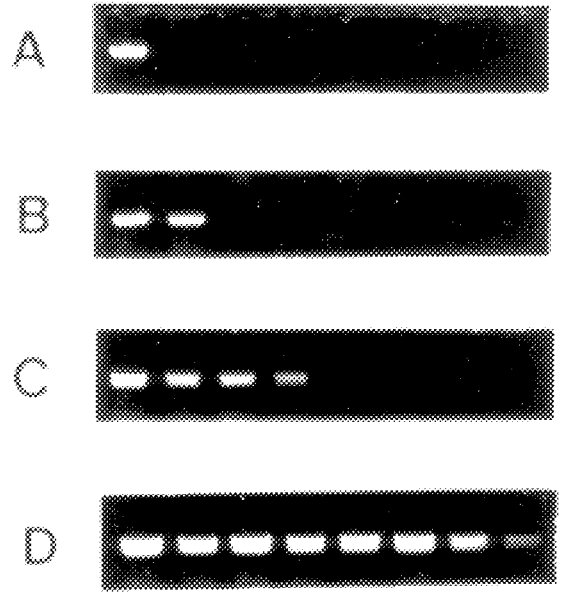
FIG. 4 is a photograph showing agarose gel electrophoresis pattern of the PCR products amplified with lyophilized PCR mixtures containing stabilizers after standing at 50° C. for certain period of time.

In order to confirm whether the addition of stabilizer and lyophilization made an effect on the heat stability of PCR mixture, storage at 50° C. was applied to a conventional aqueous reaction mixture free of stabilizer, an aqueous reaction mixture containing 20 mM ammonium sulfate, a lyophilized reaction mixture and a lyophilized reaction mixture containing 100 mM glucitol, respectively. PCR was performed at every 12 hrs in the same manner as in Example 1 and PCR products thus amplified were electrophoresed as aboves(see: FIG. 4). In FIG. 4, A, B, C and D represent the conventional aqueous reaction mixture without stabilizer, the reaction mixture containing 20 mM ammonium sulfate, the lyophilized reaction mixture and the lyophilized reaction mixture containing 100 mM glucitol, respectively; and, lanes 1 to 8 represent PCR products amplified after storage of 12 hrs, 24 hrs, 36 hrs, 50 hrs, 62 hrs, 86 hrs, 112 hrs and 136 hrs, respectively. As can be seen in FIG. 4, B, C and D revealed the maintenance of heat stability over 12 hrs, 24 hrs and 120 hrs, respectively, as compared with the aqueous reaction mixture free of stabilizer(A). Accordingly, it could be concluded that the addition of stabilizer and lyophilization resulted in heat stability of a PCR mixture Glucitol which is a polyol, conferred the most improved heat stability on the lyophilized PCR mixture.

EXAMPLE 6

Figure 5:
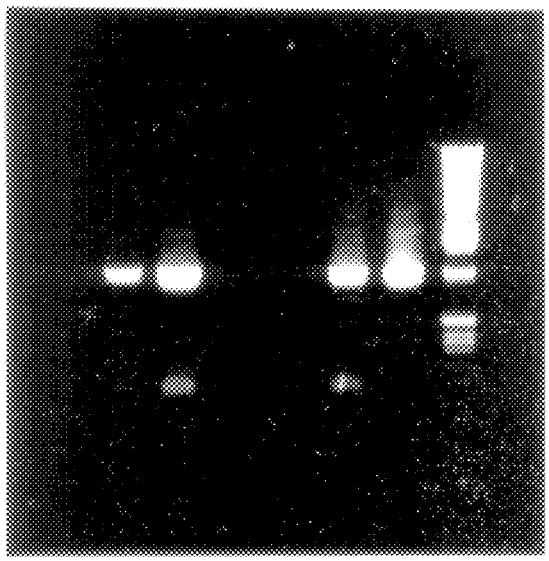
FIG. 5 is a photograph showing agarose gel electrophoresis pattern of the PCR products amplified with lyophilized PCR mixtures containing polyol as a stabilizer after storage at 50° C. for 62 hrs.

Improvement of Heat Stability of the Lyophilized PCR Mixture by the Addition of Polyols In order to examine the improvement of stability of the lyophilized PCR mixture by the addition of polyols, the lyophilized reaction mixtures containing 20 mM of glucose, mannitol, galacitol or glucitol as a stabilizer were subject to standing at 50° C. for 62 hours. PCR was carried out in the same manner as in Example 1 and PCR products thus amplified were electrophoresed as aboves(see: FIG. 5).

In FIG. 5, lanes 1 to 4 are PCR products amplified by the lyophilized reaction mixtures containing 20 mM of glucose, mannitol, galacitol and glucitol, respectively; and, lane M is 1 kb ladder as molecular marker. As can be seen in FIG. 5, all the lanes showed a distinct band corresponding to 1 kb DNA fragment of interest. Accordingly, it was clearly demonstrated that polyols improved heat stability of the lyophilized PCR mixture.

EXAMPLE 7

Effect of Water-Soluble Dye on PCR

Figure 6:
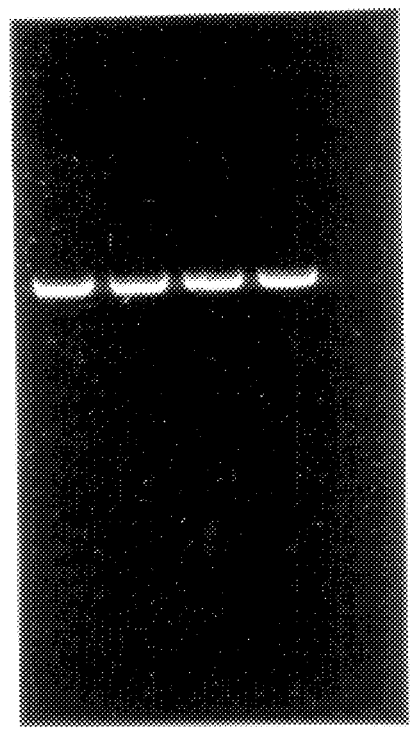
FIG. 6 is a photograph showing agarose gel electrophoresis pattern of the PCR products amplified with lyophilized PCR mixtures containing water-soluble dyes; and, FIG. 7 is a photograph showing the results of nucleotide sequence analysis by empolying the PCR reagent of the invention.

In order to identify the existence of the lyophilized PCR reagent and to ensure complete mixing of the PCR reagent and test sample, water-soluble dyes such as bromophenol blue, xylene cyanole, bromocresol red, methyl green, and cresol red were added to the conventional PCR mixture of Example 1 to the final concentration of 0.01% (v/v) and then freeze-dried. The PCR followed and their products thus amplified were electrophoresed on agarose gel(see: FIG. 6).

In FIG. 6, lanes 1 to 5 are PCR products amplified by the lyophilized PCR mixtures containing bromophenol blue, xylene cyanole, bromocresol red, cresol red and methyl green, respectively. As seen in FIG. 6, there was no decrease in the level of PCR, except for the case of methyl green-added reaction mixture. This result validates that bromophenol blue, xylene cyanole, bromocresol red and cresol red can be efficiently added in the preparation of the lyophilized PCR mixtures.

From the results from Examples 1 to 7, it was determined that the PCR reagent of the invention prepared by freeze-drying an aqueous PCR mixture which comprises stabilizer or water-soluble dye, was heat-stabilized in a great deal and maintained the DNA polymerase activity even under a high temperature. Accordingly, the PCR reagent of the present invention was applied to a kit for analysis of nucleotide sequence as described in Example 8.

EXAMPLE 8

Determination of DNA Sequence

In order to determine nucleotide sequence, 30 $\mu$M of ddGTP, 300 $\mu$M of ddATP, 400 $\mu$M of ddTTP or 200 $\mu$M of ddCTP was added to four tubes each of which contains a PCR mixture comprising 10 $\mu$M of dNTPs, 50 mM of Tris-HCl, 1.5 mM of $MgCl_2$, DNA polymerase, 5 pmoles of universal primer(5'-CGCCAGGGTTTTCCCAGTCACGAC-3') and 100 mM of glucitol as a stabilizer. The mixtures thus prepared were lyophilized and left at a constant temperature for 12 hours. Then, tubes containing lyophilized mixture were resuspended with distilled water and 0.5 $\mu$g of template DNA (pUC9) was added for initiation of PCR. The thermocyclic method was employed in the PCR for DNA sequencing, in which 35 cycles of denaturation(94° C., 30 seconds), annealing(45° C., 30 seconds) and extension(72° C., 60 seconds) were carried out; and, the PCR products were electrophoresed and the silver staining followed(see: Bassam, B. J. and Anolles, G. C., Applied Biochemistry and Biotechnology, 42:181–188(1993)).

Figure 7:
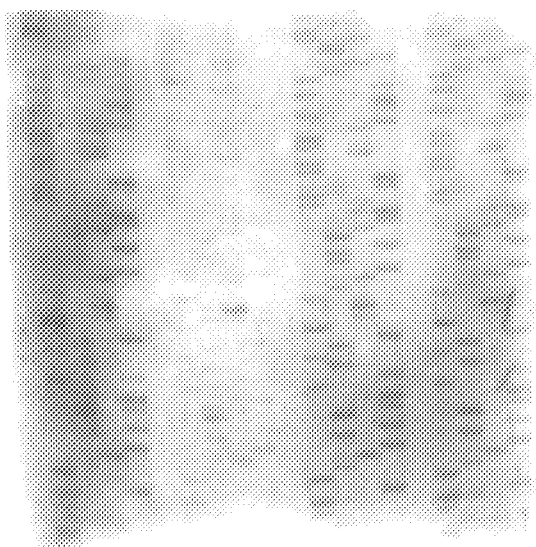

FIG. 7 is a photograph showing the results of nucleotide sequence analysis. In FIG. 7, lanes 1 & 2 and 3 & 4 represent the PCR results of the lyophilized reaction mixtures with no stabilizer(control) and the lyophilized ones with stabilizer (i.e., glucitol); and, lanes 1 & 3 and 2 & 4 show the results of nucleotide sequencing after standing for 12 hrs at −20° C. and 50° C. after lyophilization, respectively. As shown in lanes 2 and 4 of FIG. 7, the lyophilized PCR mixture containing a stabilizer maintained the DNA polymerase activity for over 12 hours at 50° C.

In this experiment, experimental data could be obtained in a reproducible and rapid manner, since DNA sequencing could be directly carried out by simply adding a template DNA to each of lyophilized PCR mixture containing ddGTP, ddATP, ddTTP or ddCTP.

As clearly illustrated and demonstrated above, the present invention provides a process for preparing an instant reagent for PCR, which comprises the steps of adding a stabilizer to the PCR mixture containing a reaction buffer, $MgCl_2$, dNTPs and a DNA polymerase, and then lyophilizing thereof. The lyophilized PCR reagent of the present invention leads to a simplification of multi-step PCR manipulation, an increase of heat stability of the reaction mixture, prevention of carry-over contamination, and improved credibility of experiments. The lyophilized PCR reagent can be used in a kit for analysis of DNA sequences or for diagnosis of diseases, which guarantees the results of high credibility in a short period of time.

What is claimed is:

1. A lyophilized and room temperature stable polymerase chain reaction reagent which is prepared by lyophilizing an aqueous reaction mixture comprising a reaction buffer, $MgCl_2$, dNTPs, a DNA polymerase, a stabilizing and sedimenting agent selected from the group consisting of glucitol and glucose, a water soluble dye selected from the group consisting of bromophenol blue, xylene cyanole, bromocresol red, and cresol red, and a primer.

2. The lyophilized and room temperature stable polymerase chain reaction reagent of claim 1 wherein said aqueous reaction mixture also comprises ddATP, ddCTP, ddGTP, or ddTTP.

* * * * *